(12) United States Patent
Großhauser et al.

(10) Patent No.: US 7,874,031 B2
(45) Date of Patent: Jan. 25, 2011

(54) PATIENT POSITIONING APPARATUS FOR A MAGNETIC RESONANCE DEVICE

(75) Inventors: Carsten Großhauser, Erlangen (DE); Herbert Weiler, Alling (DE)

(73) Assignee: Siemens Aktiengesellschaft, Munich (DE)

( * ) Notice: Subject to any disclaimer, the term of this patent is extended or adjusted under 35 U.S.C. 154(b) by 40 days.

(21) Appl. No.: 12/077,816

(22) Filed: Mar. 20, 2008

(65) Prior Publication Data
US 2008/0235874 A1    Oct. 2, 2008

(30) Foreign Application Priority Data
Mar. 27, 2007    (DE)    ........................ 10 2007 014 648

(51) Int. Cl.
*A47B 13/00*    (2006.01)
(52) U.S. Cl. .................... 5/601; 5/600; 5/943; 378/209
(58) Field of Classification Search ................... 5/601, 5/600, 943; 378/209, 196; 600/410, 415
See application file for complete search history.

(56) References Cited

U.S. PATENT DOCUMENTS

| 5,210,893 | A | 5/1993 | Uosaki et al. |
| 5,272,776 | A | 12/1993 | Kitamura |
| 5,490,297 | A | 2/1996 | Bradcovich et al. |
| 6,195,578 | B1 | 2/2001 | Distler et al. |
| 6,460,206 | B1 * | 10/2002 | Blasche et al. ................. 5/601 |
| 6,776,527 | B1 * | 8/2004 | Tybinkowski et al. ....... 378/209 |
| 2005/0034237 | A1 * | 2/2005 | Lenting et al. ................. 5/600 |
| 2005/0204472 | A1 * | 9/2005 | Gagneur et al. ................ 5/601 |
| 2006/0167356 | A1 * | 7/2006 | Everett et al. ............... 600/407 |

FOREIGN PATENT DOCUMENTS

| DE | 29900512 U1 | 6/1999 |
| DE | 102004042314 A1 | 3/2006 |

OTHER PUBLICATIONS

German Office Action dated Jun. 5, 2008 for DE 10 2007 014 648. 7-35 with English translation.

* cited by examiner

Primary Examiner—Robert G Santos
Assistant Examiner—Brittany M Wilson
(74) Attorney, Agent, or Firm—Brinks, Hofer, Gilson & Lione

(57) ABSTRACT

A patient positioning apparatus for a magnetic resonance device is provided. The patient positioning apparatus includes a positioning unit with a fixing side for fixing to the magnetic resonance device, a supporting frame extending horizontally starting from the fixing side and being arranged in a vertically adjustable fashion on the positioning unit, a patient plate mounted in a moveable fashion on the supporting frame, and a vertical adjusting mechanism operable to vertically adjust the supporting frame, the vertical adjusting mechanism has a first drive motor disposed on a side within the supporting frame that is remote from the fixing side.

19 Claims, 3 Drawing Sheets

PATIENT POSITIONING APPARATUS FOR A MAGNETIC RESONANCE DEVICE

The present patent document claims the benefit of the filing date of DE 10 2007 014 648.7, filed Mar. 27, 2007, which is hereby incorporated by reference.

BACKGROUND

The present embodiments relate to a patient positioning apparatus for a magnetic resonance apparatus.

Magnetic resonance (MR) tomography is an imaging method for displaying structures inside the body of a patient. Magnetic resonance tomography is based on the physical phenomenon of nuclear magnetic resonance and has been used within the fields of medicine and biophysics. Sectional images of the body may be generated using magnetic resonance tomography. Organ and multiple organ changes may be assessed using the sectional images of the body.

Magnetic resonance tomography examination is performed using an MR installation (system), which may include a tubular magnetic resonance device that generates a strong magnetic field and a patient positioning apparatus for introducing the patient into the magnetic resonance device. The patient positioning apparatus is generally stationary and mechanically coupled to the magnetic resonance device. A stationary patient positioning apparatus includes a horizontal patient couch (support) or a horizontal supporting frame, which is fixed to the base by a column or stand and can be adjusted vertically. As an alternative to the column or stand, a positioning unit may be provided in the region of the magnetic resonance device, on which the supporting frame is mounted in a moveable fashion and by which the supporting frame can be adjusted in terms of height. A patient plate or bed may be used to move the patient in and out of the magnetic resonance device horizontally. The patient plate is moveable along the supporting frame.

The motor drive for adjusting the patient positioning apparatus and the motor drive for moving the patient plate are disposed away from the magnetic resonance device because the magnetic resonance device generates an electromagnetic field. The motor drive for the vertical adjustment of the supporting frame is generally arranged in the column supporting the patient positioning apparatus or in the positioning unit positioned on the side of the opening of the tubular magnetic resonance device.

U.S. Pat. No. 6,195,578 B1 discloses a patient positioning table for a magnetic resonance installation (system). The patient positioning table has a board, which is fastened to the patient positioning table by a motor-driven locking device and can be introduced into a tube of the magnetic resonance installation. The patient positioning table is fixed to one side of a column that may be rotated about a vertical axis, such that the patient positioning table may be pivoted and adjusted in the height direction.

SUMMARY AND DESCRIPTION

The present embodiments may obviate one or more of the drawbacks or limitations inherent in the related art. For example, the operation of a patient positioning apparatus for a magnetic resonance device may be substantially free of interference. In another example, a magnetic resonance device includes a patient positioning apparatus for operation that is substantially free of interference.

In one embodiment, a patient positioning apparatus for a magnetic resonance device includes a positioning unit, a supporting frame, and a patient plate. The positioning unit has a fixing side for fixing (attaching) to the magnetic resonance device. The supporting frame extends substantially horizontal starting from the fixing side and is arranged in a vertically adjustable fashion on the positioning unit. The patient plate is mounted in a displaceable fashion on the supporting frame. A vertical adjusting mechanism may vertically adjust the supporting frame. The vertical adjusting mechanism includes a first drive motor, which is arranged on a side within the supporting frame that is remote from the fixing side.

The "side . . . remote from the fixing side" is the region from the supporting frame, which is disposed, for example, in the last third and/or in direct proximity to a limiting wall of the supporting frame which faces the fixing side.

In one embodiment, a distance separates the drive motor and the magnetic resonance device. The drive motor is disposed on the remote side within the supporting frame. The function of the drive motor is not or is only insignificantly influenced by the electromagnetic field of the magnetic resonance device. The drive within the supporting frame has a minimal space requirement, since the drive motor is not disposed in the positioning unit. The positioning unit may only include some of the mechanical components of the adjusting mechanism. Accordingly, the positioning unit may have a reduced width. The supporting frame may be mounted with one end on the positioning unit and the other end freely suspended. The connection between the supporting frame and the positioning unit may be the only support point of the supporting frame, so that no further supporting apparatuses, such as columns or stands, are provided, starting from the fixing side. The supporting frame is accessible.

The positioning unit may connect to the magnetic resonance device. The magnetic resonance device may be central with respect to an axis of rotation of the magnetic resonance device. The positioning unit may have an essentially symmetrical design with respect to the axis of rotation of the magnetic resonance device, so that the patient positioning apparatus and/or the patient are accessible from both sides of the patient positioning apparatus.

In one embodiment, the vertical adjusting mechanism includes a spindle attached within the positioning unit, which is coupled to the first drive motor by a transmission, such as a belt drive. The spindle translates a rotation of the drive motor into a vertical adjustment movement of the supporting frame. The spindle may be positioned close to the magnetic resonance device, so that the positioning unit has a relatively small width.

In one embodiment, the spindle is coupled to the transmission in the region of its upper end by a spindle screw. With this embodiment of the adjusting mechanism, the spindle is rotated as it were so that the spindle screw is disposed in the upper region of the cylindrical rod of the shaft. The spindle screw may be disposed within the supporting frame or directly below the supporting frame, so that the spindle screw is coupled to the drive motor by simple adjusting elements, which are disposed in the supporting frame.

To guide the supporting frame along the height of the positioning unit, the vertical adjusting mechanism may include linear guides on both sides of the supporting frame in the positioning unit. The linear guides form additional support points, on which the supporting frame rests against the positioning unit and the loads on the spindle may be reduced. The linear guides provide substantially friction-free translatory movement of the supporting frame during its height adjustment.

A horizontal adjusting mechanism for adjusting the patient, which mechanism is placed in relation to the supporting frame, may include a second drive motor. The second drive motor may be disposed on the side within the supporting frame which is remote from the magnetic resonance device. The second drive motor may provide interference-free operation, since it is disposed, like the first drive motor, at an adequate distance from the magnetic resonance device. In one embodiment, all electromotors, which are provided to adjust the patient plate are disposed as far away from the coils of the magnetic resonance device as possible.

In one embodiment, the second drive motor is coupled to the patient plate by a transmission, such as a belt drive. The second drive motor in the supporting frame directly below the patient plate allows a constructively simple connection of the second drive motor to the patient plate. The connection may be a flexible drive, such as a belt drive.

The horizontal adjusting mechanism may be disposed centrally within the supporting frame. The adjusting mechanism may be connected to the patient plate at at least two points. The patient plate may be arranged centrally with respect to the longitudinal direction of the patient plate. A symmetrical distribution of the forces introduced into the patient plate occurs, so that a minimum power of the second drive motor is necessary in order to move the patient plate.

In one embodiment, the supporting frame may include rolling elements. The rolling elements may be a type of roller, which are arranged in two rows on both sides of the horizontal adjusting mechanism. Other forms of rolling elements may be used, such as balls or needles. Linear friction bearings or rail guides may also be used for a sliding guide of the patient plate. The rolling elements may reduce the friction caused during movement of the patient plate and facilitate the relative movement of the patient plate in relation to the supporting frame.

In one embodiment, the fixing side may include holes for recesses of adjusting screws. The holes may be provided on the fixing side of the positioning unit for a three-dimensional adjustable fixing of the patient positioning apparatus to the magnetic resonance device. A plurality of holes may be provided to receive a plurality of adjusting screws, which are distributed symmetrically at different heights and cover as large a surface of the fixing side as possible. The plurality of holes and adjusting screws may provide a stable connection of the patient positioning apparatus to the magnetic resonance device.

A magnetic resonance device may include a patient positioning apparatus according to one of the aforementioned embodiments. The arrangements and advantages specified with respect to the patient positioning apparatus and embodiments are to be applied equally to the magnetic resonance device.

BRIEF DESCRIPTION OF THE DRAWINGS

An exemplary embodiment is described in more detail with reference to a drawing, in which.

DETAILED DESCRIPTION

Figure 1:
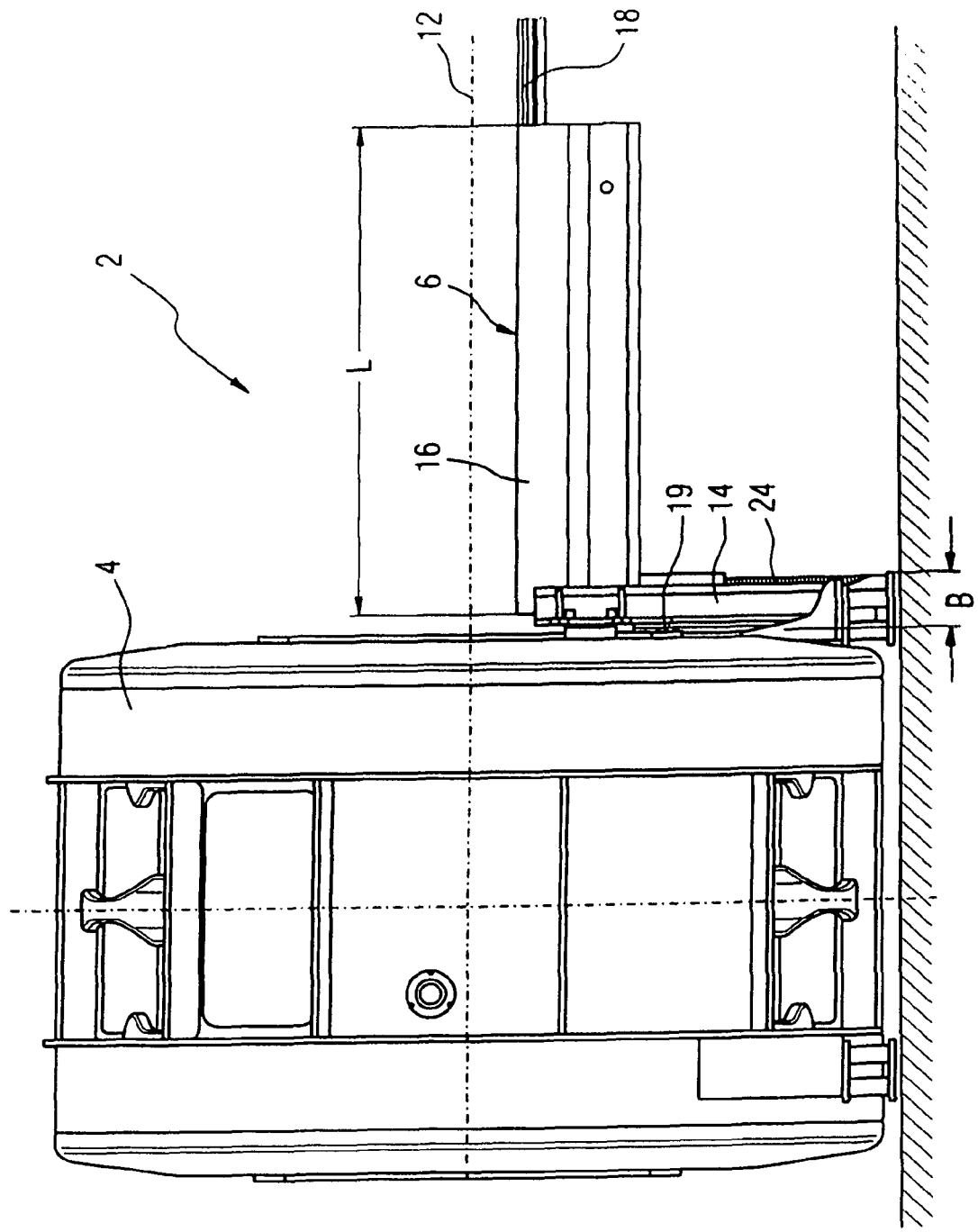
FIG. 1 shows a side view of one embodiment of a magnetic resonance installation.
Figure 2:
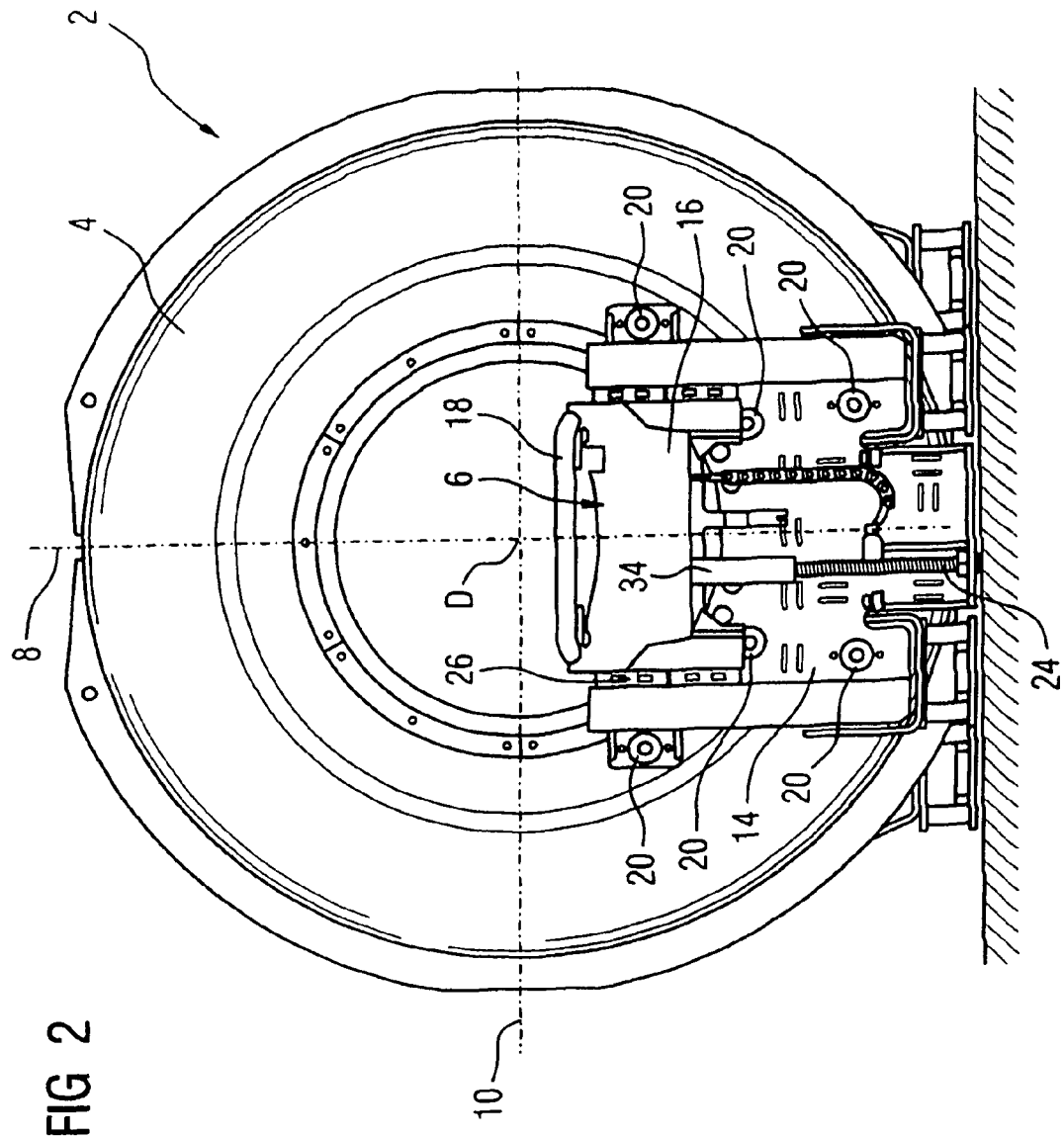
FIG. 2 shows a front view of the magnetic resonance installation as shown in FIG. 1.

FIG. 1 and FIG. 2 show a magnetic resonance installation (system) 2, which is used for medical imaging of the inside of a body of a patient. The magnetic resonance installation 2 includes a tubular magnetic resonance device 4 and a patient positioning apparatus 6. The tubular magnetic resonance device 4 may generate a strong magnetic field. The patient positioning apparatus 6 may be used to move the patient into the magnetic resonance device 4 for image recording purposes. The magnetic resonance device 4 has a rotation center D, which is formed by the intersection point of a vertical axis 8 and a transverse axis 10 (see FIG. 2). The magnetic resonance device 2 has a longitudinal axis 12, along which the patient can be moved with the aid of the patient positioning apparatus 6.

In one embodiment, the patient positioning apparatus 6 includes a vertical positioning unit 14, a supporting frame 16, and a patient plate 18. The patient plate 18 may be mounted in a moveable fashion in the longitudinal direction 12 on the supporting frame 16. The positioning unit 14 includes a fixing side that faces the magnetic resonance device 4, with the supporting frame 16 extending horizontally in the longitudinal direction 12 starting from the fixing side 19. The vertical positioning unit 14 is fastened (fixed) here to the magnetic resonance device 4 in an adjustable fashion along all three axes 8, 10 and 12 by six adjusting screws 20, which are screwed into the holes 22 on the fixing side 19 (see FIG. 3). The positioning unit 14 remains stationary after it has been fixed to the magnetic resonance device 4.

The patient positioning apparatus 6 is embodied such that the positioning unit 14 has an essentially symmetrical design and is connected centrally to the magnetic resonance device 4 with respect to the vertical axis 8 and/or the pivot point D, with the positioning unit 14 not protruding beyond the contour of the magnetic resonance device 4 in the transverse direction 10, as shown from the front in FIG. 2. The positioning unit 14 has a width B in the longitudinal direction 12, which is much smaller than a length L of the supporting frame 16 in the same direction. The minimal dimensioning and symmetrical design of the positioning unit 14 on both sides of the patient plate 18 provides particularly good and almost unrestricted accessibility to the patient plate 18 and/or the patient resting thereupon.

The supporting frame 16 may be mounted on the positioning unit such that the supporting frame 16 is movable in the vertical direction 8. A vertical adjusting mechanism may move the supporting frame 16 in the vertical direction 8. The vertical adjusting mechanism includes a drive motor 28, a transmission associated therewith (see FIG. 3), a spindle 24, which translates the rotational movement of the drive motor 28 into a translatory (translational) vertical movement of the supporting frame 16, and linear guides 26 arranged on both sides of the supporting frame 16 within the positioning unit 14.

Figure 3:
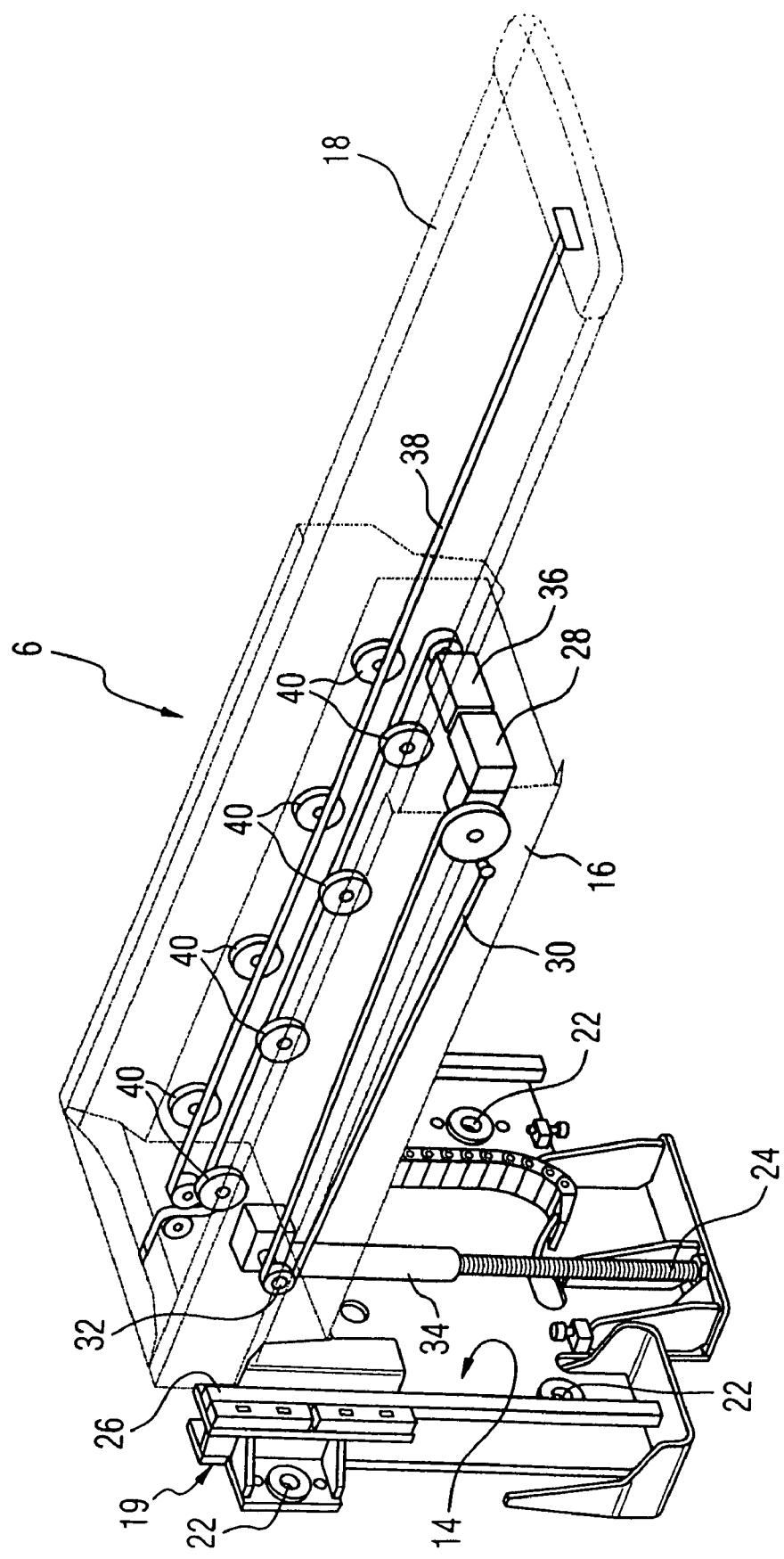
FIG. 3 shows a perspective view of one embodiment of a patient positioning apparatus with the patient plate and supporting frame shown transparently.

In FIG. 3, a first drive motor 28 is arranged inside the supporting frame 16 on a side remote from the fixing side 19. The rotation of the drive motor 28 is transferred to a shaft 32 on the drive side by a belt 30. The shaft 32 is connected on its side to a spindle screw 34 arranged in the region of the upper end of the spindle 24 by drive elements. The rotation of the drive motor 28 over the spindle 24 effects a vertical adjustment of the supporting arm 16, with the patient plate 18 being moved between a rising height to raise and lower the patient and an entry height for introduction into the magnetic resonance device 4.

A second drive motor 36 may be arranged in the region of the supporting frame 16, remote from the fixing side 19, which borders the first drive motor 28. The drive motor 36 is part of a horizontal adjusting mechanism for moving the patient plate 18 in the longitudinal direction 12. The rotation of the second drive motor 36 is converted into a translatory movement of the patient plate 18 along the longitudinal axis 12 by a belt 38, which is positioned centrally in the supporting frame 16 and is connected to the patient plate 18 in the region of the two distal ends of the patient plate 18.

In one embodiment, the supporting frame 16 may include rolling elements. As shown in FIG. 3, two rows of rolling elements may be arranged on both sides of the horizontal adjusting mechanism in the supporting frame 16. The rolling elements may be rollers 40. The rollers 40 may be used to slide the patient plate 18 with minimum friction, during longitudinal movement.

In one embodiment, the drive motors 28 and 36 are attached, within the supporting frame 16, to a side remote from the fixing side 19. The drive motors 28 and 36 are disposed at a distance from the magnetic resonance device 4, such that the influence of the strong magnetic field generated in the magnetic resonance device 4 is minimized. All or some of the components of the vertical and the horizontal adjusting mechanism are arranged in the supporting frame 16 or in the positioning unit 14, such that a stand or column arranged on the side of the supporting frame is not needed, in which in particular components of the vertical adjusting mechanism are accommodated.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A patient positioning apparatus for a magnetic resonance device, the apparatus comprising:
   a positioning unit with a fixing side extending in a vertical direction for fixing to the magnetic resonance device, wherein the positioning unit is operable to remain stationary after being fixed to the magnetic resonance device,
   a supporting frame extending horizontally and away from the magnetic resonance device, starting from the fixing side and being arranged in a vertically adjustable fashion on the positioning unit,
   a patient plate mounted in a moveable fashion on the supporting frame, and
   a vertical adjusting mechanism operable to vertically adjust the supporting frame, the vertical adjusting mechanism having a first drive motor disposed on a side within the supporting frame that is remote from the fixing side.

2. The patient positioning apparatus as claimed in claim 1, wherein the positioning unit connects to the magnetic resonance device, which is central with respect to an axis of rotation of the magnetic resonance device.

3. The patient positioning apparatus as claimed in claim 1, wherein the vertical adjusting mechanism includes a spindle disposed within the positioning unit, the spindle being coupled to the first drive motor by a transmission.

4. The patient positioning apparatus as claimed in claim 3, wherein an upper end of the spindle is coupled to the transmission by a spindle screw.

5. The patient positioning apparatus as claimed in claim 3, wherein the transmission is a belt drive.

6. The patient positioning apparatus as claimed in claim 3, wherein the vertical adjusting mechanism includes linear guides on both sides of the supporting frame in the positioning unit.

7. The patient positioning apparatus as claimed in claim 6, wherein a horizontal adjusting mechanism for adjusting the patient plate with respect to the supporting frame comprises a second drive motor disposed on a side within the supporting frame that is remote from the magnetic resonance device.

8. The patient positioning apparatus as claimed in claim 7, wherein the fixing side of the positioning unit includes holes for receiving adjusting screws for the adjustable fixing of the positioning unit to the magnetic resonance device.

9. The patient positioning apparatus as claimed in claim 1, wherein the vertical adjusting mechanism includes linear guides on both sides of the supporting frame in the positioning unit.

10. The patient positioning apparatus as claimed in claim 1, wherein a horizontal adjusting mechanism for adjusting the patient plate with respect to the supporting frame comprises a second drive motor disposed on a side within the supporting frame that is remote from the magnetic resonance device.

11. The patient positioning apparatus as claimed in claim 10, wherein the second drive motor is coupled to the patient plate by a transmission.

12. The patient positioning apparatus as claimed in claim 11, wherein the transmission is a belt drive.

13. The patient positioning apparatus as claimed in claim 10, wherein the horizontal adjusting mechanism is disposed centrally within the supporting frame.

14. The patient positioning apparatus as claimed in claim 10, wherein the supporting frame includes rolling elements for moving the patient plate.

15. The patient positioning apparatus as claimed in claim 1, wherein the fixing side of the positioning unit includes holes for receiving adjusting screws for the adjustable fixing of the positioning unit to the magnetic resonance device.

16. The patient positioning apparatus as claimed in claim 1, wherein a vertical-extending first end of a supporting frame is mounted on the positioning unit and a second end, which is opposite the first end, is freely suspended.

17. The patient positioning apparatus as claimed in claim 16, wherein a connection between the supporting frame and the positioning unit is the only support point of the supporting frame, so that no further supporting apparatuses are provided starting from the fixing side.

18. The patient positioning apparatus as claimed in claim 1, wherein the fixing side extending in the vertical direction faces the magnetic resonance device.

19. A magnetic resonance device comprising:
   a patient positioning apparatus including:
      a positioning unit with a fixing side extending in a vertical direction for fixing to the magnetic resonance device, wherein the positioning unit is operable to remain stationary after being fixed to the magnetic resonance device,
      a supporting frame extending horizontally and away from the magnetic resonance device, starting from the fixing side and being arranged in a vertically adjustable fashion on the positioning unit,
      a patient plate mounted in a moveable fashion on the supporting frame, and
      a vertical adjusting mechanism operable to vertically adjust the supporting frame, the vertical adjusting mechanism having a first drive motor disposed on a side within the supporting frame that is remote from the fixing side.

* * * * *